US00PP34292P2

(12) United States Plant Patent
Wood

(10) Patent No.: US PP34,292 P2
(45) Date of Patent: Jun. 7, 2022

(54) ***THUJA* PLANT NAMED 'SMNTOO'**

(50) Latin Name: *Thuja occidentalis*
Varietal Denomination: SMNTOO

(71) Applicant: Timothy D. Wood, Spring Lake, MI (US)

(72) Inventor: Timothy D. Wood, Spring Lake, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 0 days.

(21) Appl. No.: 17/492,638

(22) Filed: Oct. 3, 2021

(51) Int. Cl.
*A01H 7/00* (2006.01)
*A01H 6/00* (2018.01)

(52) U.S. Cl.
USPC ..... Plt./213
CPC ..... *A01H 6/00* (2018.05)

(58) Field of Classification Search
USPC ..... Plt./213
CPC ..... A01H 5/12; A01H 7/00
See application file for complete search history.

*Primary Examiner* — Kent L Bell
(74) *Attorney, Agent, or Firm* — C. Anne Whealy

(57) ABSTRACT

A new and distinct cultivar of *Thuja* plant named 'SMNTOO', characterized by its upright plant habit; narrow columnar plant form; vigorous growth habit; moderate growth rate; dense and bushy form; branchlets that are twisting; bright green-colored leaves; bright green coloration maintained during the winter; and good winter hardiness.

2 Drawing Sheets

Figure 1:
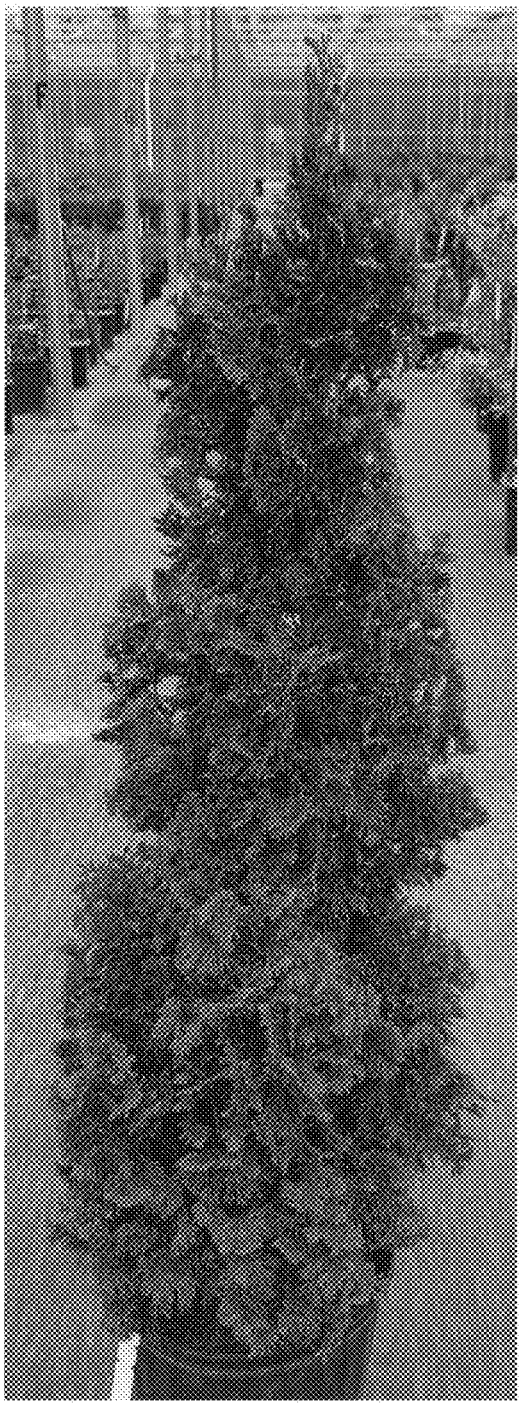

Botanical designation: *Thuja occidentalis.*
Cultivar denomination: 'SMNTOO'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Thuja* plant, botanically known as *Thuja occidentalis*, commonly known as American Arborvitae and hereinafter referred to by the name 'SMNTOO'.

The new *Thuja* plant is a product of a planned breeding program conducted by the Inventor in Grand Haven, Mich. The objective of the breeding program was to develop new *Thuja* plants with a upright narrow plant habit and attractive foliage.

The new *Thuja* plant originated from an open-pollination in 2000 of the *Thuja occidentalis* 'Degroot's Spire', not patented, as the female, or seed parent and an unknown selection of *Thuja occidentalis* as the male, or pollen, parent. The new *Thuja* plant was discovered and selected by the Inventor in 2016 as a plant within the progeny of the stated open-pollination in a controlled outdoor nursery environment in Grand Haven, Mich.

Asexual reproduction of the new *Thuja* plant by softwood stem cuttings in a controlled environment in Grand Haven, Mich. since 2016, has shown that the unique features of this new *Thuja* plant are stable and reproduced true to type in successive generations.

SUMMARY OF THE INVENTION

Plants of the new *Thuja* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNTOO'. These characteristics in combination distinguish 'SMNTOO' as a new and distinct *Thuja* plant:

1. Upright plant habit; narrow columnar plant form.
2. Vigorous growth habit; moderate growth rate.
3. Dense and bushy form.
4. Branchlets that are twisting.
5. Bright green-colored leaves; bright green coloration maintained during the winter.
6. Good winter hardiness.

Plants of the new *Thuja* can be compared to plants of the female parent, 'Degroot's Spire'. Plants of the new *Thuja* differ primarily from plants of 'Degroot's Spire' in the following characteristics:

1. Plants of the new *Thuja* are narrower from base to apex than plants of 'Degroot's Spire'.
2. Branchlets of plants of the new *Thuja* are more twisting than branchlets of plants of 'Degroot's Spire'.

Plants of the new *Thuja* can also be compared to plants of *Thuja occidentalis*, 'Art Boe', disclosed in U.S. Plant Pat. No. 22,174. In side-by-side comparisons, plants of the new *Thuja* differ primarily from plants of 'Art Boe' in the following characteristics:

1. Plants of the new *Thuja* are narrower than plants of 'Art Boe'.
2. Branchlets of plants of the new *Thuja* are more twisting than branchlets of plants of 'Art Boe'.

BRIEF DESCRIPTION OF THE PHOTOGRAPHS

The accompanying colored photographs illustrate the overall appearance of the new *Thuja* plant showing the colors as true as it is reasonably possible to obtain in colored reproductions of this type. Colors in the photographs may differ slightly from the color values cited in the detailed botanical description which accurately describe the colors of the new *Thuja* plant.

The photograph on the first sheet (FIG. 1) is a side perspective view of a typical plant of 'SMNTOO'.

Figure 2:
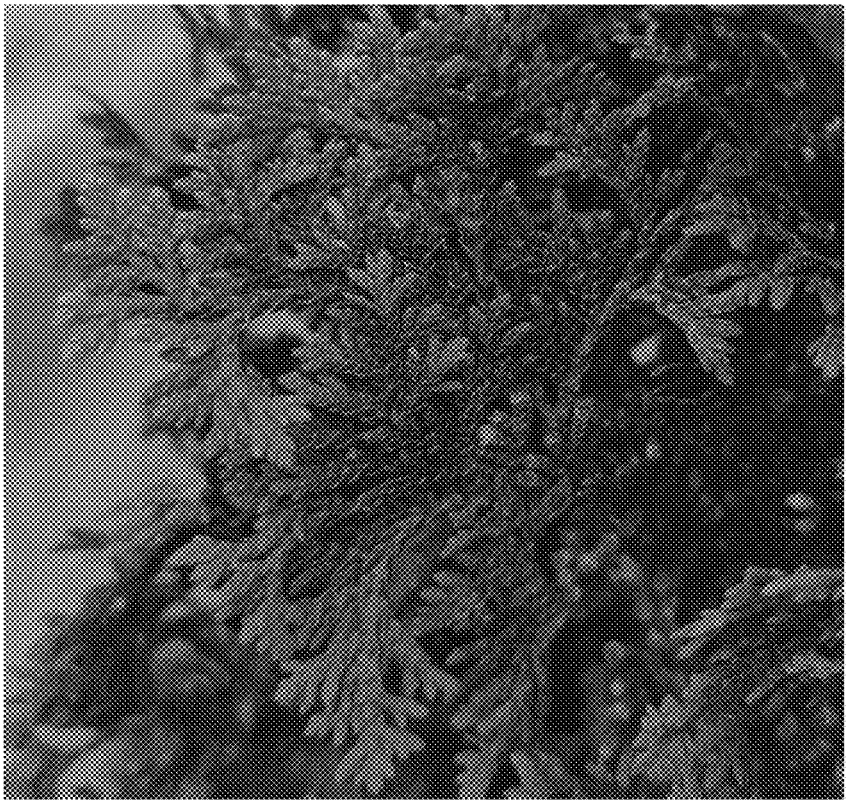

The photograph on the second sheet (FIG. 2) is a close-up view of a typical plant of 'SMNTOO'.

DETAILED BOTANICAL DESCRIPTION

The aforementioned photographs and following observations, measurements and values describe plants grown in the spring in three-gallon containers in a polypropylene-covered shadehouse in Grand Haven, Mich. and under cultural practices typical of commercial *Thuja* production. During the production of the plants, day temperatures ranged from 18° C. to 27° C. and night temperatures ranged from 5° C. to 10° C. Plants were three years old when the photographs and the description were taken. In the description, color references are made to The Royal Horticultural Society Colour Chart, 2015 Edition, except where general terms of ordinary dictionary significance are used.

Botanical classification: *Thuja occidentalis* 'SMNTOO'.

Parentage:

*Female, or seed, parent.*—*Thuja occidentalis* 'Degroot's Spire', not patented.

*Male, or pollen, parent.*—Unknown selection of *Thuja occidentalis*, not patented.

Propagation:

*Type.*—By softwood stem cuttings.

*Time to initiate roots, summer.*—About 45 days at temperatures about 10° C. to 27° C.

*Time to produce rooted young plants, summer.*—About six months at temperatures about 10° C. to 27° C.

*Root description.*—Thick to fine; fibrous; typically white and tan in color, actual color of the roots is dependent on substrate composition, water quality, fertilizer, substrate temperature and physiological age of roots.

*Rooting habit.*—Freely branching; medium density.

Plant description:

*Plant and growth habit.*—Perennial evergreen shrub; upright plant habit and narrowly columnar plant form; vigorous growth habit; moderate growth rate.

*Plant height.*—About 100 cm.

*Plant diameter, base.*—About 25 cm to 30 cm.

*Branching habit.*—Freely branching habit with about 50 to 75 lateral branches developing per plant; dense and bushy habit.

*Lateral branch description.*—Length: About 20 cm. Diameter: About 4 mm. Internode length: About 1 cm. Aspect: Main branch, upright; lateral branches about 20° to 45° from stem axis. Strength: Strong. Texture, developing branches: Scaly; glabrous. Texture, main trunk: Woody. Color: Close to N200A.

*Leaf description.*—Appearance and arrangement: Flattened and closely appressed, scale-like; opposite, simple; sessile. Length: About 1.5 mm. Width: About 1 mm. Shape: Ovate. Apex: Acuminate. Base: Truncate. Margin: Entire. Venation pattern: Parallel. Texture: Rough, glabrous; coriaceous; waxy. Fragrance: Aromatic and cedar-like. Color: Developing leaves, upper and lower surfaces: Close to 143C. Fully expanded leaves, upper and lower surfaces: Close to NN137B; venation, close to NN137B.

Cone description: To date, cone development has not been observed on plants of the new *Thuja*.

Garden performance: Plants of the new *Thuja* have been observed have good garden performance and good winter hardiness.

Pathogen & pest resistance: Plants of the new *Thuja* have been observed to be resistant to root rot pathogens. Plants of the new *Thuja* have not been observed to be resistant to pests and other pathogens common to *Thuja* plants.

It is claimed:

1. A new and distinct *Thuja* plant named 'SMNTOO' as illustrated and described.

* * * * *